US010433113B2

United States Patent
DeAngelis et al.

(10) Patent No.: US 10,433,113 B2
(45) Date of Patent: Oct. 1, 2019

(54) SYSTEM AND METHOD FOR DETERMINING SPLIT-TIMES IN A RELAY RACE

(71) Applicant: ISOLYNX, LLC, Haverhill, MA (US)

(72) Inventors: Douglas J. DeAngelis, Ipswich, MA (US); Edward G. Evansen, West Newbury, MA (US)

(73) Assignee: ISOLYNX, LLC, Haverhill, MA (US)

( * ) Notice: Subject to any disclaimer, the term of this patent is extended or adjusted under 35 U.S.C. 154(b) by 0 days.

(21) Appl. No.: 15/454,773

(22) Filed: Mar. 9, 2017

(65) Prior Publication Data
US 2017/0259156 A1    Sep. 14, 2017

Related U.S. Application Data

(60) Provisional application No. 62/305,813, filed on Mar. 9, 2016.

(51) Int. Cl.
*A61B 5/00* (2006.01)
*H04W 4/02* (2018.01)
(Continued)

(52) U.S. Cl.
CPC .......... *H04W 4/027* (2013.01); *A61B 5/1114* (2013.01); *A61B 5/1126* (2013.01);
(Continued)

(58) Field of Classification Search
CPC ........ A63B 71/0686; A63K 3/00; A63K 1/00; H04W 4/027; A61B 5/1114;
(Continued)

(56) References Cited

U.S. PATENT DOCUMENTS

| 4,008,892 A | 2/1977 | Nissen |
| 4,156,870 A * | 5/1979 | Desarzens ................ G07C 1/24 340/323 R |

(Continued)

FOREIGN PATENT DOCUMENTS

| WO | WO 2014/197575 | 12/2014 |
| WO | WO 2014/197618 | 12/2014 |

(Continued)

OTHER PUBLICATIONS

WIkipedia Article on Relay Races, https://en.wikipedia.org/wiki/Relay_race, printed 30 May 18.*

(Continued)

*Primary Examiner* — Corbett B Coburn
(74) *Attorney, Agent, or Firm* — Lathrop Gage LLP

(57) ABSTRACT

A method for determining split-times in a relay race run using one or more lanes of a running track, where a relay team in each lane carries a respective relay baton, includes, for each lane: (a) periodically determining a location of the respective relay baton, (b) determining, for one or more take-over zones in the lane, respective first times when the relay baton crosses a respective line within the take-over zone, (c) determining a second time when a finish line of the relay race is reached, and (d) determining a split-time for each segment of the relay race, based upon a start time of the relay race, the one or more first times, and the second time.

9 Claims, 5 Drawing Sheets

(51) Int. Cl.
*A61B 5/11* (2006.01)
*A63K 1/00* (2006.01)
*G06K 9/00* (2006.01)
*G07C 1/00* (2006.01)
*G07C 1/24* (2006.01)

(52) U.S. Cl.
CPC .......... *A61B 5/6825* (2013.01); *A61B 5/6895* (2013.01); *A63K 1/00* (2013.01); *G06K 9/00342* (2013.01); *G07C 1/00* (2013.01); *G07C 1/24* (2013.01); *A61B 5/002* (2013.01); *A61B 5/112* (2013.01); *A61B 5/1112* (2013.01); *A61B 2503/10* (2013.01); *A61B 2562/0219* (2013.01)

(58) Field of Classification Search
CPC ... A61B 5/1126; A61B 5/6825; A61B 5/6895; A61B 5/002; A61B 5/1112; A61B 5/112; A61B 2503/10; A61B 2562/0219; G06K 9/00342; G07C 1/00; G07C 1/24
See application file for complete search history.

(56) References Cited

U.S. PATENT DOCUMENTS

| | | | |
|---|---|---|---|
| 5,917,351 | A | 6/1999 | Shiue et al. |
| 7,381,058 | B1 | 6/2008 | Hayes, Sr. |
| 8,989,880 | B2 | 3/2015 | Wohl et al. |
| 9,002,485 | B2 | 4/2015 | Wohl et al. |
| 9,014,830 | B2 | 4/2015 | Wohl et al. |
| 9,126,094 | B1* | 9/2015 | Davis .................. G07C 1/24 |
| 9,180,357 | B2 | 11/2015 | Richley |
| 9,517,417 | B2 | 12/2016 | Austerlade et al. |
| 9,531,415 | B2 | 12/2016 | Stelfox et al. |
| 9,571,143 | B2 | 2/2017 | Richley |
| 9,602,152 | B2 | 3/2017 | Wohl et al. |
| 9,667,287 | B2 | 5/2017 | Richley |
| 9,698,841 | B2 | 7/2017 | Alonso et al. |
| 9,699,278 | B2 | 7/2017 | Richley et al. |
| 9,715,005 | B2 | 7/2017 | Hughes et al. |
| 9,742,450 | B2 | 8/2017 | O'Hagan et al. |
| 2005/0202905 | A1 | 9/2005 | Chesser |
| 2005/0203714 | A9* | 9/2005 | Vincenzini ............ G07C 1/24 702/150 |
| 2008/0074954 | A1* | 3/2008 | Moritani .............. G04F 10/00 368/113 |
| 2009/0079570 | A1 | 3/2009 | Yarsa et al. |
| 2009/0147025 | A1* | 6/2009 | Grigsby ............. H04N 21/2187 345/633 |
| 2009/0213700 | A1* | 8/2009 | Conant .................. G04F 8/08 368/113 |
| 2012/0163340 | A1* | 6/2012 | Chin ................ H04W 36/0088 370/331 |
| 2013/0325525 | A1* | 12/2013 | Boyd, Jr. .......... G06Q 30/0631 705/5 |
| 2013/0342699 | A1 | 12/2013 | Hansen et al. |
| 2014/0018944 | A1* | 1/2014 | Ko ....................... G07C 1/24 700/91 |
| 2014/0184207 | A1* | 7/2014 | Rosenmoeller .... A63B 71/0605 324/207.22 |
| 2014/0320660 | A1 | 10/2014 | DeAngelis et al. |
| 2014/0361875 | A1 | 12/2014 | O'Hagan et al. |
| 2014/0361890 | A1 | 12/2014 | O'Hagan et al. |
| 2014/0361906 | A1 | 12/2014 | Hughes et al. |
| 2014/0362120 | A1 | 12/2014 | Wohl et al. |
| 2014/0364973 | A1 | 12/2014 | O'Hagan et al. |
| 2014/0364977 | A1 | 12/2014 | Wohl et al. |
| 2014/0365194 | A1 | 12/2014 | O'Hagan et al. |
| 2014/0365415 | A1 | 12/2014 | Stelfox et al. |
| 2014/0365639 | A1 | 12/2014 | Wohl et al. |
| 2014/0365640 | A1 | 12/2014 | Wohl et al. |
| 2015/0134143 | A1* | 5/2015 | Willenborg .......... G05D 1/0094 701/2 |
| 2015/0149250 | A1 | 5/2015 | Fein et al. |
| 2015/0149837 | A1 | 5/2015 | Alonso et al. |
| 2015/0151183 | A1 | 6/2015 | Lapides |
| 2015/0178817 | A1 | 6/2015 | Fein et al. |
| 2015/0312494 | A1 | 10/2015 | Aldridge et al. |
| 2015/0335952 | A1 | 11/2015 | Wohl et al. |
| 2015/0335953 | A1 | 11/2015 | Wohl et al. |
| 2015/0335954 | A1 | 11/2015 | Wohl et al. |
| 2015/0378002 | A1 | 12/2015 | Hughes et al. |
| 2016/0045159 | A1 | 2/2016 | Balakrishnan et al. |
| 2016/0361595 | A1 | 12/2016 | O'Hagan et al. |
| 2017/0043260 | A1 | 2/2017 | Austerlade et al. |
| 2017/0056721 | A1 | 3/2017 | Stelfox et al. |
| 2017/0173387 | A1 | 6/2017 | Wohl et al. |
| 2017/0257127 | A1 | 9/2017 | Alonso et al. |
| 2017/0272556 | A1 | 9/2017 | Richley et al. |
| 2017/0317702 | A1 | 11/2017 | O'Hagan et al. |
| 2017/0361198 | A1* | 12/2017 | Medina-Brodsky ................. A63B 71/0686 |

FOREIGN PATENT DOCUMENTS

| | | |
|---|---|---|
| WO | WO 2014/197623 | 12/2014 |
| WO | WO 2014/197679 | 12/2014 |
| WO | WO 2016/196863 | 12/2016 |

OTHER PUBLICATIONS

International Search Report with Written Opinion corresponding to International Patent Application No. PCT/US2017/021620, dated Jul. 3, 2017, 15 pages.
International Preliminary Report on Patentability (Chapter II) dated May 2, 2018 for International Patent Application PCT/US17/21620—23 pages.

* cited by examiner

| SPLIT TIMES 450 | | | | |
|---|---|---|---|---|
| LANE | FIRST LEG | SECOND LEG | THIRD LEG | LAST LEG |
| 1 | 10.98 | 10.14 | 10.25 | 9.69 |
| 2 | 10.24 | 10.54 | 10.35 | 10.47 |
| 3 | 9.98 | 10.14 | 10.17 | 10.78 |
| 4 | 10.54 | 10.22 | 10.83 | 10.07 |
| 5 | 10.10 | 10.31 | 10.39 | 10.70 |

SYSTEM AND METHOD FOR DETERMINING SPLIT-TIMES IN A RELAY RACE

CROSS-REFERENCE TO RELATED APPLICATIONS

The present application claims the benefit of priority from U.S. Provisional Application Ser. No. 62/305,813 filed Mar. 9, 2016, which is incorporated herein by reference in its entirety.

BACKGROUND

In a relay race around a running track, the starting position and relay take-over zones for each relay team are staggered depending upon the lane being run and such that each team covers the same distance when they cross the finish line. Such staggered start positions and staggered relay take-over zones make measurement of split times for each competitor very difficult.

U.S. Patent Application Publication Number 2005/0203714 A9 illustrates timing and position of contestants on a track using at least one set of two trapezoidal shaped loops that have a longitudinal axes that project from an inside rail to an outside rail on the track. Each competitor has at least one communication device and remote base station is in communication with the positioning device, wherein the positioning device determines a contestant time as the contestant passes the wire loop and also determines the position of the contestant in relation to an inside guide such as a rail. However, this approach clearly does not work for races where the athletes run in lanes and thus have staggered distance points on the track.

DETAILED DESCRIPTION OF THE EMBODIMENTS

Figure 1:
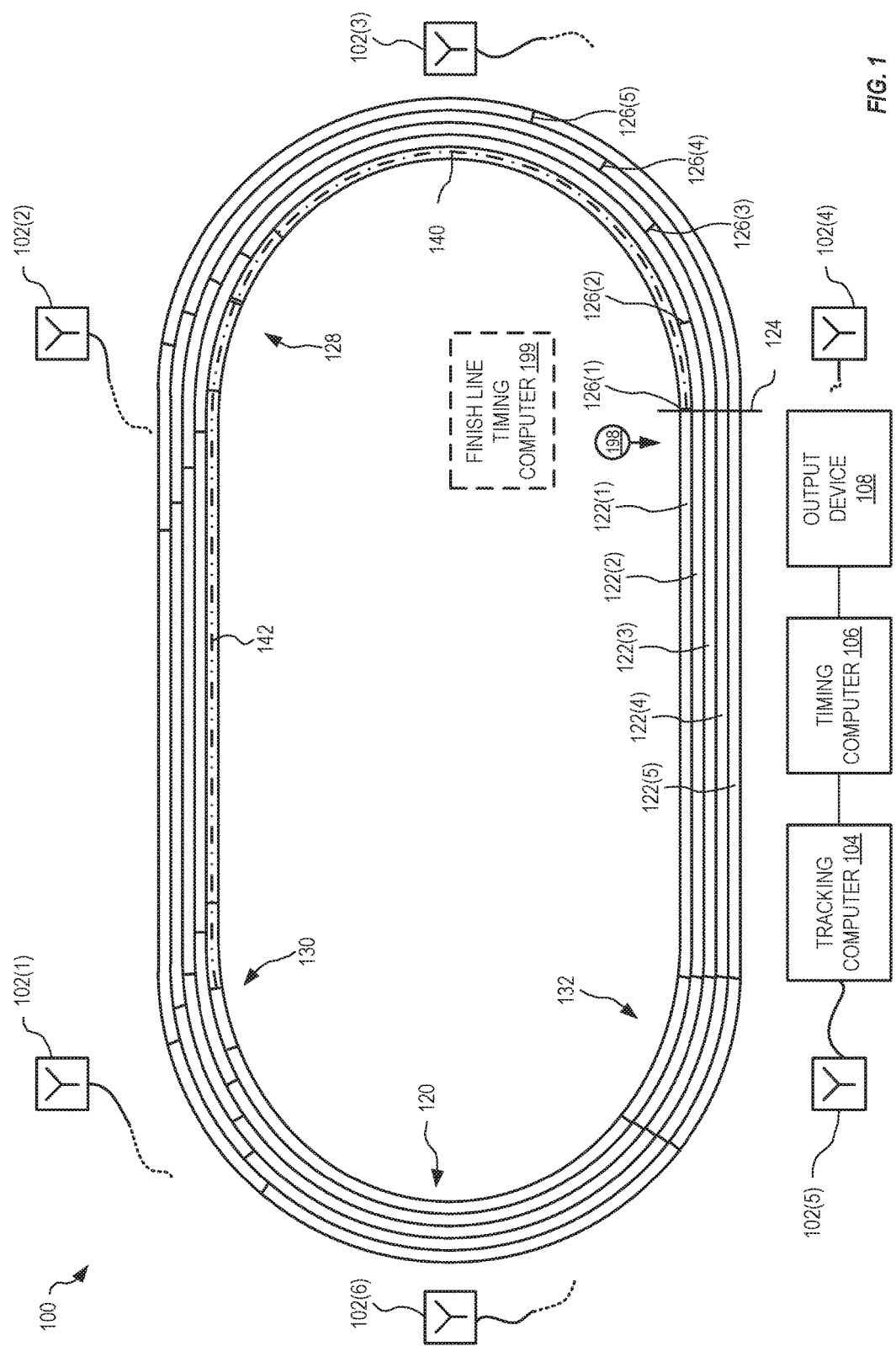
FIG. 1 shows one system for determining split-times in a relay race run around a running track, in an embodiment.
Figure 2:
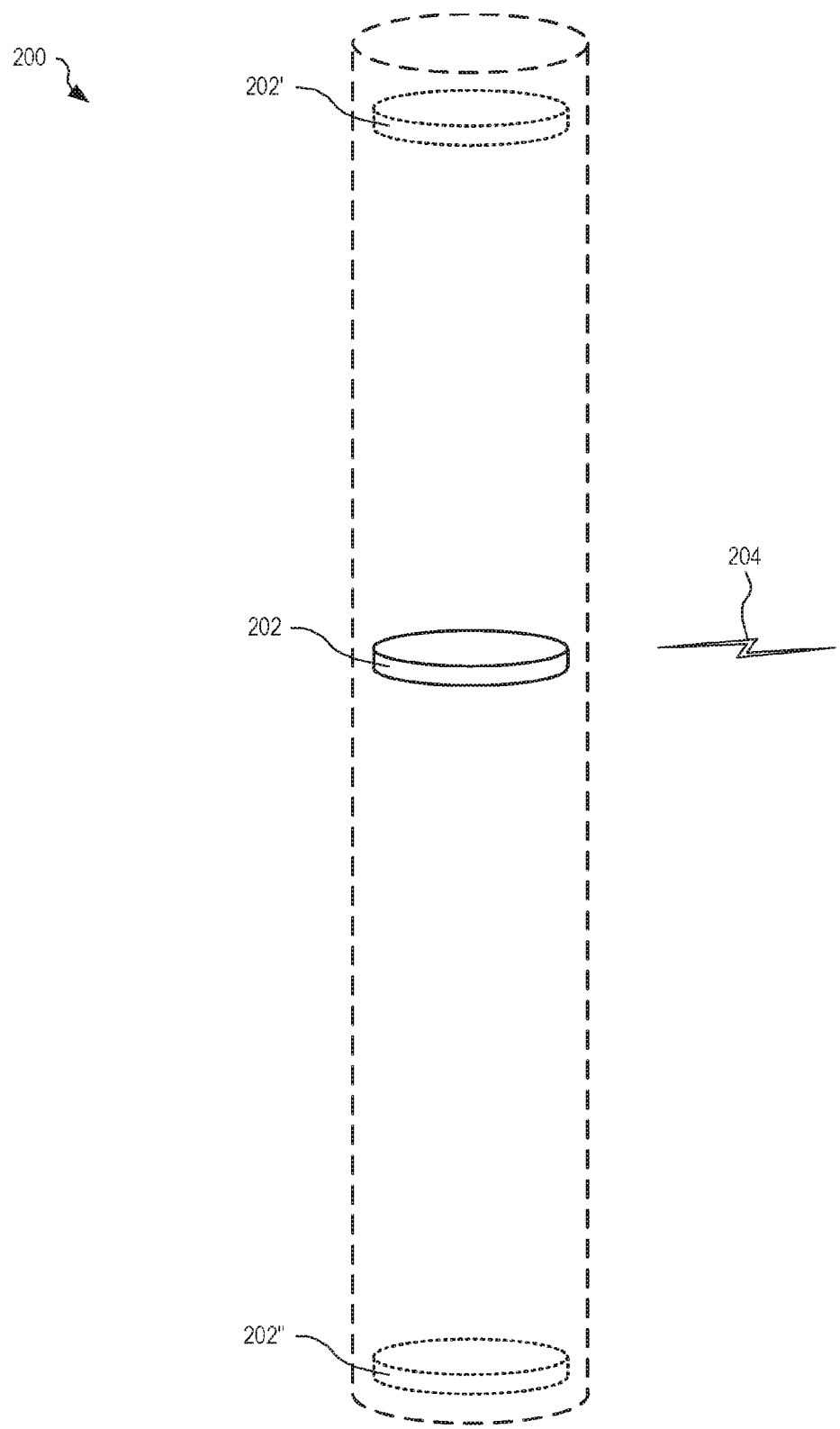
FIG. 2 shows one relay baton configured with a wireless tracking tag, in an embodiment.
Figure 3:
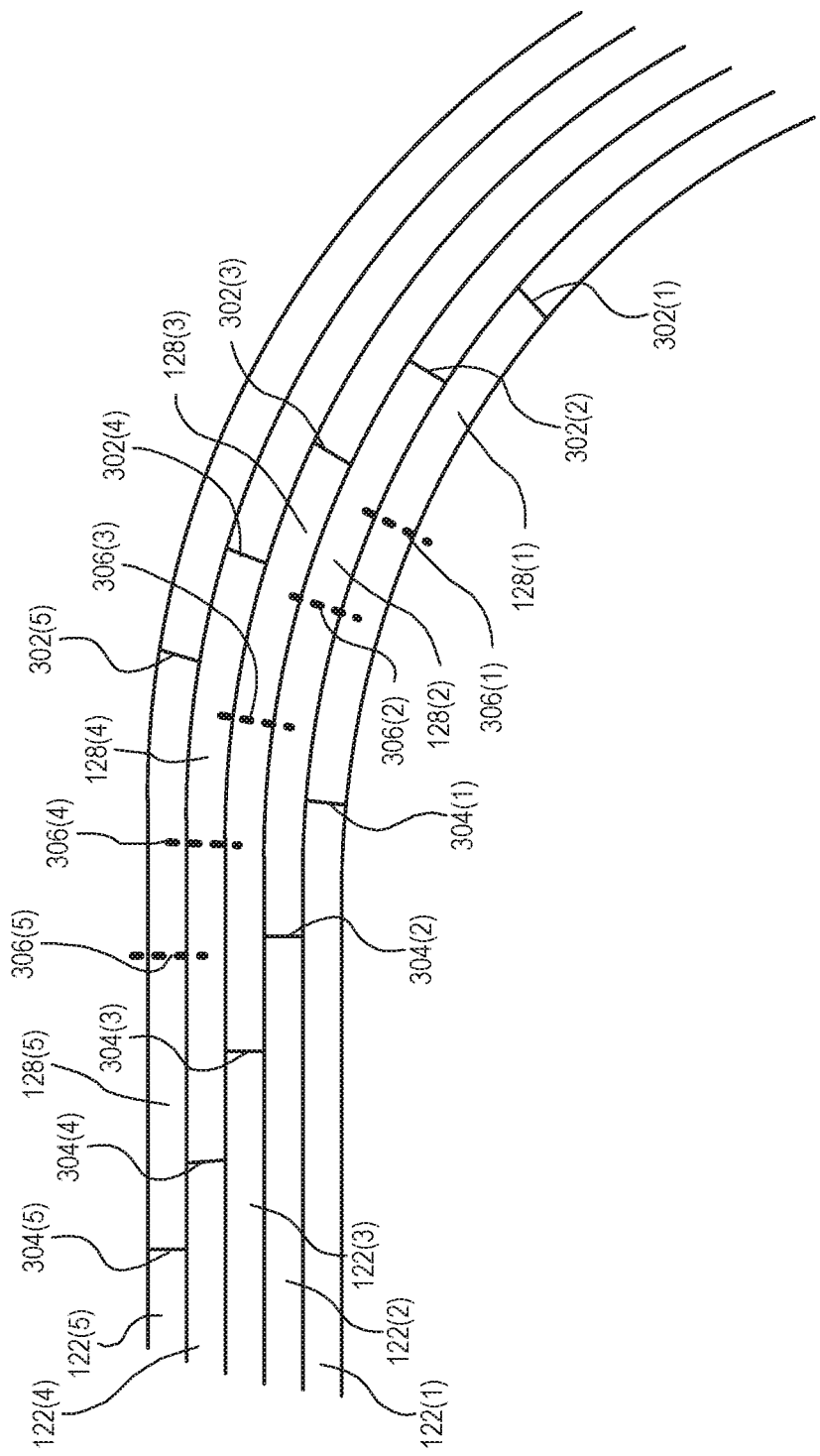
FIG. 3 shows a portion of the track of FIG. 1 illustrating the first take-over zones of the track of FIG. 1.
Figures 4, 5:
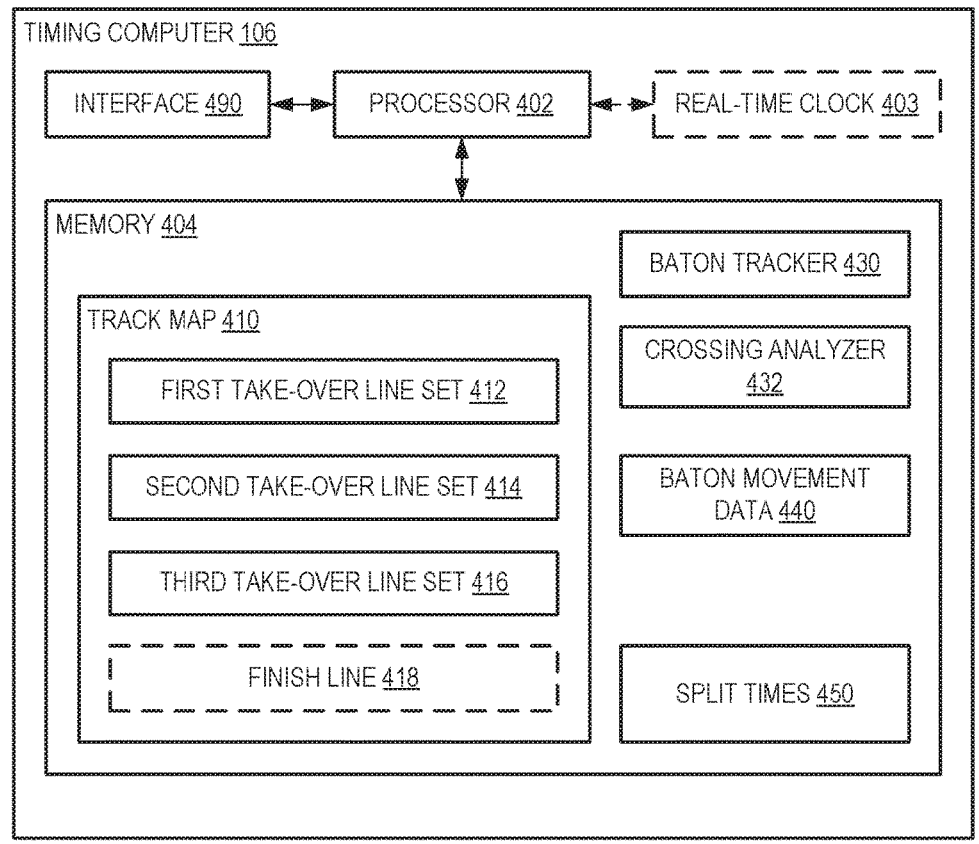
FIG. 4 shows the timing computer of FIG. 1 in further exemplary detail.
FIG. 5 shows one split-time table, in an embodiment.

FIG. 1 shows one system 100 for determining split-times in a relay race run around a running track 120. FIG. 2 shows one exemplary relay baton 200 configured with a wireless tracking tag 202. FIG. 3 shows a portion of track 120 of FIG. 1 illustrating first take-over zones 128 of track 120 of FIG. 1. FIG. 4 shows a timing computer 106 of system 100 in further exemplary detail. FIGS. 1, 2, 3 and 4 are best viewed together with the following description. The following examples illustrate a four by one-hundred meter (4×100) relay race on a 400 meter track, however, other distances may be similarly timed without departing from the scope hereof.

FIG. 1 illustratively shows running track 120 with five lanes 122, a finish line 124, a plurality of staggered start positions 126, and first, second, and third staggered take-over zones 128, 130, 132, respectively, for a 4×100 relay race. In the example of FIG. 1, the relay race distance is four hundred meters, divided into four segments (legs) of approximately one hundred meters each, where each of four athletes of a relay team runs a different one of the segments in one of the lanes. For each relay race, one baton (e.g., baton 200) is assigned to each lane 122 of track 120 (i.e., one baton to each relay team).

In FIG. 1, a first segment of lane 122(1) is indicated by dashed line 140 and a second segment of lane 122(1) is indicated by dashed-dotted line 142. The first athlete of the team runs the first segment carrying a relay baton, and passes the baton to the second athlete, who runs the second segment. The second athlete passes the baton to the third athlete who runs the third segment. The third athlete passes the baton to the fourth athlete who finishes the race. The baton is passed between athletes as they run within take-over zones 128, 130, and 132 of each lane.

As shown in FIG. 3, for each lane 122(1)-(5), take-over zone 128 has zone start markers 302(1)-(5) and zone end markers 304(1)-(5), where the previous segment ends and the next segment starts at a line 306(1)-(5) of each take-over zones 128, respectively. Although not shown, take-over zones 130 and 132 have similar lines 306 for each lane 122. For each lane 122 and each take-over zone 128, 130, and 132, line 306 is within the take-over zone, for example but not necessarily at the mid-point of the take-over zone. As shown in FIG. 3, these lines 306 do not form a single straight line across all lanes, and therefore a conventional timing system that requires crossing of a single straight line is unable to determine when athletes cross these lines 306. Thus, conventional timing systems are unable to perform split timing of the relay race. Rather, to perform split timing of the relay race, system 100 uses the crossing of each line 306 for each lane 122, and finish line 124 to determine timing for each segment of the relay race.

However, since athletes are accelerating and decelerating within take-over zones 128 as batons (e.g., baton 200) are passed therebetween, system 100 determines split-times based upon when each baton crosses corresponding lines 306.

As shown in FIG. 2, each relay baton 200 is configured with at least one wireless tag 202 (e.g., an ultra-wideband transmitter) that is configured to periodically (e.g., between once every 5 ms and once every 100 ms, such as once every 50 ms) transmit a wireless signal 204 (hereinafter ping 204) that includes unique identification information of the tag 202 and/or baton 200. In one embodiment, baton 200 is configured with two tags 202' and 202" each positioned at a different end of baton 200 such that ping 204 is less likely to be blocked by the athlete holding the baton. Without departing from the scope hereof, wireless tag 202 may transmit wireless signal at non-periodic intervals, e.g., quasi-periodic intervals, or aperiodic intervals.

System 100 includes at least three wireless receivers 102 (e.g., six are shown in FIG. 1) positioned around track 120 such that each ping 204 is received in at least three receivers 102 as batons 200 are carried around track 120. Receivers 102 are time synchronized and record information (e.g., data transmitted within ping 204 and received signal strength of ping 204) of ping 204 together with a time of arrival of ping 204 at the receiver. Each receiver 102 is communicatively coupled (wired and/or wirelessly) with a tracking computer 104 that receives, for each ping 204, the ping information, the time of arrival of each ping 204 to receiver 102, and identification of receiver 102. Tracking computer 104 is for example a computer that includes software (known in the art) that is executed by a processor to determine a location of baton 200 within track 120 based upon known (predetermined) location of each receiver 102 relative to track 120 and the time of arrival of each transmitted ping 204 at each receiver 102. Thus, for each tracked baton 200, tracking computer 104 periodically (e.g., every 50 ms or less) determines a location of baton 200 relative to track 120.

Tracking computer 104 is communicatively coupled (wired and/or wirelessly) with a timing computer 106 that utilizes the periodically determined locations of batons 200 relative to track 120 to calculate split-times 450 of the athletes participating in the relay race around track 120. Without departing from the scope hereof, tracking computer 104 and timing computer 106 may be implemented within a single, common computer.

In one embodiment, system 100 further includes wireless tags 202 (optionally implemented as wireless tags 202' and 202"). In another embodiment, system 100 further includes batons 200 coupled with wireless tags 202 (optionally implemented as a wireless tag 202' and a wireless tag 202" in each baton 200).

As shown in FIG. 4, timing computer 106 is a computer that includes at least one processor 402 communicatively coupled with memory 404. Timing computer 106 may also include a real-time clock 403. Memory 404 is non-transitory and is configured to store a track map 410 that defines the location of at least lines 306 and finish line 124 of track 120. Timing computer 106 may be supplied to a user with track map 410 preloaded in memory 404. Alternatively, track map 410 may be loaded onto timing computer 106 by a user, for example in situations requiring a venue- or event-specific track map 410. In an embodiment (not illustrated in FIG. 4), track map 410 is automatically created based on reference tags placed around track 120. For example, placement of eight reference tags, one at each side of the finish line, one at each end of the straightaway and one at each apex of the curve, is sufficient to map track entirely 120, including all exchange zones in every lane 122 for most common relay formats. Timing computer 106 includes an interface 490 and is configured to receive, via interface 490, a start signal 198 from a finish line timing computer 199 that operates to time races on track 120, wherein start signal 198 indicates the start of the relay race and timing computer 106 starts (and/or resets to zero) real-time clock 403. Optionally, timing computer 106 may also receive, via interface 490, finish line timing information from finish line timing computer 199. Without departing from the scope hereof, timing computer 106 may receive start signal 198 and finish line timing information from two different respective systems.

In a typical 400 meter outdoor track, track map 410 defines three sets of take-over lines: a first take-over line set 412, a second take-over line set 414, and a third take-over line set 416. First take-over line set 412 defines one line for each lane 122, where each line corresponds to a respective one of lines 306 of take-over zones 128. Second take-over line set 414 defines one line for each lane 122, where each line corresponds to a respective one of lines 306 of take-over zones 130. Third take-over line set 416 defines one line for each lane 122, where each line corresponds to a respective one of lines 306 of take-over zones 132. Optionally, track map 410 further defines a finish line 418. Finish line 418 represents the location of finish line 124 across all lanes 122. This example of track map 410 is readily extended to other track configurations, for example tracks having a different length and/or a different number of take-over zones.

Timing computer 106 includes software, implemented as machine readable instructions stored in memory 404 that, when executed by processor 402, provide functionality of timing computer 106 described herein. This software includes a baton tracker 430 and a crossing analyzer 432. Baton tracker 430 concurrently tracks each baton 200, based upon location data of each baton periodically received from tracking computer 104, and determines movement (illustratively shown as baton movement data 440) for each baton 200. Baton tracker 430 periodically invokes crossing analyzer 432 to determine a time, based upon real-time clock 403 and baton movement data 440, when baton 200 crosses a corresponding line of line sets 412, 414, 416, and finish line 418. Baton tracker 430 calculates the relative time by subtracting a corresponding time of the previously crossed line, or the start time for the first segment of the race, and stores the determined split-times within split-times 450.

In one embodiment, real-time clock 403 is free running and timing computer 106 reads and stores a start time from real-time clock 403 upon receiving start signal 198, wherein subsequent times for the relay race are determined relative to the start signal by subtracting the stored start time and one or more previously-determined split-times from times read from real-time clock 403.

System 100 may also determine other metric of each athlete. For example, system 100 may determine a speed of each baton 200, and thereby a speed of the athlete carrying the baton. Wireless tag 202 (or 202') may include an accelerometer, allowing stride frequency to be reported and associated length to be calculated based on baton speed.

Optionally, baton tracker 430 includes one or more filters that operate to smooth determined movement of baton 200, such that movement variations caused by swinging of the athlete's arm carrying the baton are filtered out. For example, where an athlete takes less than fifty strides to cover one hundred meters and system 100 determines the location of baton 200 at least twenty times per second, the determined location data would show that baton 200 slows down as the athlete's arm carrying the baton moves backwards, and accelerates as the athlete's arm carrying the baton moves forward for each stride. This variation occurs at about five hertz or lower and could thus be removed using a filter. However, it is noted that as the baton is exchanged between athletes, the athletes' arms become more stable in relation to their bodies as they reach towards each other.

In one example of operation, timing computer 106 determines split-times in a relay race run using two or more lanes 122 of running track 120. At time T0, timing computer 106 receives start signal 198 from finish line timing computer 199 and reads and either stores a time from real-time clock 403 or resets real-time clock 403 to a reference time, e.g., zero seconds or time T0. Baton tracker 430, for each baton 200 in the relay race, generates baton movement data 440 based upon location data received from tracking computer 104. Timing computer 106 periodically invokes crossing analyzer 432 to determine when, based upon movement data 440, each baton 200 crosses a corresponding line of first take-over line set 412. At time T1, crossing analyzer 432 determines that baton 200 in lane 122(1) crosses a line of first take-over line set 412 corresponding to lines 306(1) and stores the time from real-time clock 403 in a first leg column of split-times 450 (e.g. see FIG. 5) for the first lane. Baton tracker 430 continues to update baton movement data 440 and utilizes crossing analyzer 432 to determine when, based upon movement data 440, other batons 200 cross corresponding lines of first take-over line set 412, storing the determined times in the first leg column of split-times 450. Baton tracker 430 continues to update baton movement data 440 and utilizes crossing analyzer 432 to determine when, based upon movement data 440, batons 200 cross corresponding lines of second take-over line set 414, storing the determined split-times in the second leg column of split-times 450. Baton tracker 430 continues to update baton movement data 440 and utilizes crossing analyzer 432 to determine when, based upon movement data 440, batons 200 cross corresponding lines of third take-over line set 416, storing the determined split-times in the third leg column of split-times 450. Baton tracker 430 continues to update baton movement data 440 and utilizes crossing analyzer 432 to determine when, based upon movement data 440, batons 200 cross finish line 418, storing the determined split-times in the fourth leg column of split-times 450. Alternatively, timing computer 106 may receive finish line timing information from an external system, such as finish line timing computer 199, and use finish line timing information and the times when relay batons 200 crossed third take-over line set 416 to determine the split times for the fourth leg of the relay race.

FIG. 5 shows split-times table 450 containing example timing results for each athlete in each lane 122 of the relay race. Timing computer 106 may send split-times 450 to an output device 108, such as a stadium score board, a live TV feed, and/or other computerized systems. In one embodiment, timing computer 106 includes a database for storing results, split-times, and athlete information.

In one example where track 120 has eight lanes, thirty-two athletes may compete in a 4×100 relay race. System 100 tracks each athlete's running based upon movement of the corresponding relay baton 200. Because each relay team spends the entire race in its own lane, the starting lines and the first, second and third take-over zones 128, 130, 132 for all team are not in a single plane. Further, since the athletes run at different speeds, the start times for all but the first 8 athletes are all different. Effectively, the race is really thirty-two separate one-hundred meter races run over twenty five different one-hundred meter race courses (consider the last leg is the same for all) with twenty-five different start times (consider that the first start is the same for all). Thus, to achieve the split timing for all athletes, system 100 tracks each athlete's segment individually.

Figure 6:
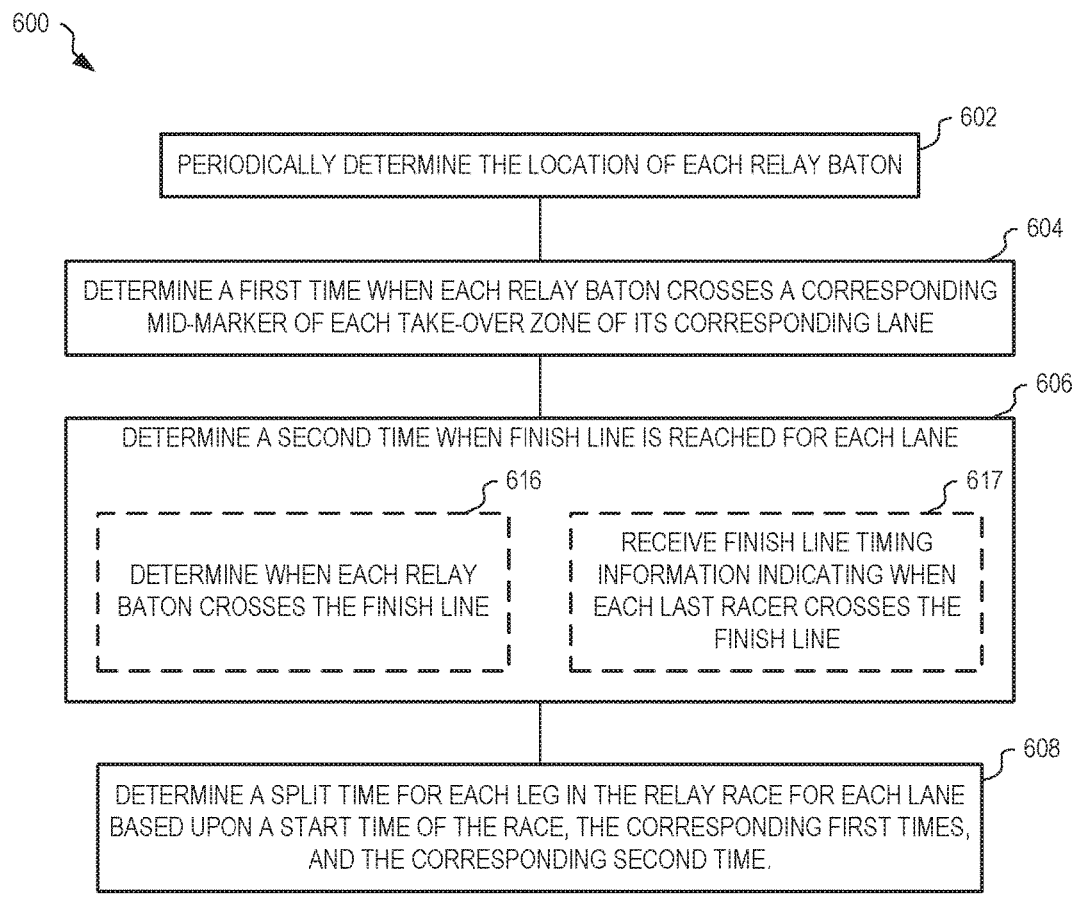
FIG. 6 is a flowchart illustrating one method for determining split-times in a relay race, in an embodiment.

FIG. 6 is a flowchart illustrating one exemplary method 600 for determining split-times in a relay race. Method 600 is implemented in timing computer 106 for example.

In step 602, method 600 periodically determines the location of each relay baton. In one example of step 602, tracking computer 104 periodically determines a location of each relay baton based upon information of ping received by receivers positioned around the running track. In step 604, method 600 determines a first time when each relay baton crosses a corresponding lines of each take-over zone of its corresponding lane. In one example of step 604, baton tracker 430 and crossing analyzer 432 determines when baton 200 crosses lines 306 of each lane 122. In step 606, method 600 determines a second time when the finish line is reached for each lane. In one embodiment, step 606 includes a step 616 of determining when each relay baton crosses the finish line. In one example of step 616, baton tracker 430 and crossing analyzer 432 determines when baton 200 crosses finish line 124. In another embodiment, step 606 includes a step 617 of receiving finish line timing information indicating when the last runner of each relay team crosses the finish line. In one example of step 617, timing computer 106 receives finish line information from finish line timing computer 199 indicating when a body part of the last runner of each relay team crosses the finish line. Finish line timing computer 199 may obtain such finish line timing information from a photo finish camera. In step 608, method 600 determines a split-time for each leg in the relay race for each lane, based upon a start time of the race, the corresponding first times and the corresponding second time. In one example of step 608, baton tracker 430 generates split-times 450 based upon a start time of the race, the determined first times and the determined second times.

Steps of method 600 may be performed in a different order without departing from the scope hereof. For example, split-times may be determined for each segment rather than waiting until the race has finished.

Although the 4×100 relay race is used in the above examples, as noted above, other races may benefit from use of system 100 for determining split times. For example, it is not uncommon to run a "three turn stagger" in a 4×400 meter relay race, where the entire first segment (leg) and the first part of the second segment (leg) are run in lanes. Similarly, many indoor relay races have the athletes run in lanes at least part of the race.

System 100 has many advantages over prior art methods for timing relay races that require sensors to be buried within the running track, since no modification of the running track is required. Advantageously, system 100 may also measure other statistical information for the athlete. For example, system 100 may determine when an athlete is accelerating or decelerating during their segment (leg) and how efficient the baton exchange is (i.e., were the athletes both running at top speed when the baton was exchanged, or did one athlete have to slow down to make the exchange).

It is understood that the systems and methods disclosed herein may locate the baton(s) using the Global Positioning System (GPS) rather than via triangulation using a plurality of receivers, without departing from the scope hereof. For example, each wireless tag 202 (or 202') may determine its location via GPS and transmit the determined location to tracking computer 104. Likewise, step 602 may utilize GPS wireless tags instead of wireless tags communicatively coupled with a plurality of receivers.

Combinations of Features

Features described above as well as those claimed below may be combined in various ways without departing from the scope hereof. For example, it will be appreciated that one system or method for determining split-times in a relay race, described herein may incorporate or swap features of another system or method for determining split-times in a relay race, described herein. The following examples illustrate some possible, non-limiting combinations of embodiments described above. It should be clear that many other changes and modifications may be made to the systems and methods herein without departing from the spirit and scope of this invention:

(A1) A method for determining split-times in a relay race run using one or more lanes of a running track, where a relay team in each lane carries a respective relay baton, may include, for each lane (a) periodically determining a location of the respective relay baton, (b) determining, for one or more take-over zones in the lane, respective first times when the relay baton crosses a respective line within the take-over zone, (c) determining a second time when a finish line of the relay race is reached, and (d) determining a split-time for each segment of the relay race, based upon a start time of the relay race, the one or more first times, and the second time.

(A2) The method denoted as (A1) may further include determining the start time of the relay race and determining, for each lane, the split time corresponding to a first segment of the relay race run.

(A3) In either or both of the methods denoted as (A1) and (A2), the step of determining a second time may include determining time of the relay baton crossing the finish line.

(A4) In the method denoted as (A3), the step of determining time of the relay baton crossing the finish line may include determining the time of the relay baton crossing the finish line based upon locations of the relay baton determined in the step of periodically determining a location.

(A5) In any of the methods denoted as (A1) through (A4), the step of determining a second time may include receiving finish line timing information indicating when last racer of the relay team crosses the finish line.

(A6) In the method denoted as (A5), the step of receiving the finish line timing information may include receiving time data indicating when a body part of the last racer crosses the finish line.

(A7) In either or both of the methods denoted as (A5) and (A6), the step of receiving the finish line timing information may include receiving time data based at least in part on a photo finish image.

(A8) Any of the methods denoted as (A1) through (A7) may further include determining a speed of one of the relay batons.

(A9) In the method denoted as (A8), the step of determining a speed may include determining the speed based upon locations of the relay baton determined in the step of periodically determining a location.

(A10) Any of the methods denoted as (A1) through (A9) may further include determining baton movement data of one of the relay batons.

(A11) The method denoted as (A10) may further include filtering the baton movement data to smooth the determined baton movement.

(A12) In either or both of the methods denoted as (A10) and (A11), the step of determining baton movement data may include determining the baton movement data based upon locations of the relay baton determined in the step of periodically determining a location.

(B1) A system for determining split-times in a relay race run, using two or more lanes of a running track and two or more respective relay batons, may include (a) a plurality of wireless tracking tags configured for coupling to the relay batons to equip each of the relay batons with at least one of the wireless tracking tags, each of the wireless tracking tags being configured to periodically emit a ping during the relay race run, (b) at least three receivers configured to be positioned at known locations relative to and around the running track and configured to receive the pings from the wireless tracking tags, wherein each receiver records time of arrival of the ping, and information content of the ping, (c) a tracking computer communicatively coupled with each of the receivers and operable to periodically determine locations of the batons relative to the receivers based on triangulation using the time of arrival and information content of at least some of the pings, and (d) a timing computer communicatively coupled with the tracking computer to determine split times for each leg of the race for each lane at least in part based upon the locations.

(B2) In the system denoted as (B1), the timing computer may be communicatively coupled with a finish line timing computer to receive therefrom at least one of (i) a start signal and (ii) finish line timing information.

(B3) In the system denoted as (B2), the timing computer may be configured to use the start signal in determination of the split time for first leg of the relay race run in each lane.

(B4) In either or both of the systems denoted as (B2) and (B3), the timing computer may be configured to use the finish line timing information in determination of the split time for last leg of the relay race run in each lane.

(B5) In any of the systems denoted as (B1) through (B4), the timing computer may include a track map specifying positions of take-over lines to enable determination of the split times at least in part through comparison of the locations relative to the take-over lines of the associated lane.

(B6) In the system denoted as (B5), the track map may further specify location of the finish line to enable determination time of completion of last leg of the relay race run in each lane based upon the locations.

(B7) Any of the systems denoted as (B1) through (B6) may further include the relay batons.

(B8) In the system denoted as (B7), each of the relay batons may be coupled with two wireless tracking tags positioned at opposite ends of the relay baton.

(B9) In any of the systems denoted as (B1) through (B8), the tracking computer may include a filter for smoothing movement of the relay batons determined from the locations.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for determining split-times of a relay race run on a running track with a plurality of lanes, each of the lanes having one or more staggered take-over zones in which a corresponding baton of said each of the lanes is handed off, the system comprising:

wireless tracking tags configured for coupling to each baton to equip each baton with at least one of the wireless tracking tags, each of the wireless tracking tags being configured to periodically emit pings during the relay race;

at least three receivers configured to be positioned at known locations around the running track and configured to receive the pings from the wireless tracking tags, wherein each of the receivers records a time of arrival and information content for each of the received pings;

a tracking computer configured to communicatively couple with the receivers to periodically determine locations of each baton relative to the running track based on the known locations of the receivers and the time of arrival and information content of at least some of the pings received from said each baton; and a timing computer that includes a real-time clock configured to output a start time in response to a start signal, the timing computer being configured to:
 (i) store a track map specifying locations of staggered take-over lines of the staggered take-over zones,
 (ii) communicatively couple with the tracking computer to receive therefrom the periodically-determined locations of each baton,
 (iii) track each baton during the relay race based on the periodically-determined locations of said each baton to determine movement of said each baton,
 (iv) obtain from the real-time clock a crossing time when each baton crosses a corresponding one of the staggered take-over lines stored in the track map, as based on the movement of said each baton, (v) determine each split time of each baton by subtracting from each crossing time of said each baton (a) a previous crossing time, when said each baton crossed a previous one of the take-over lines, and (b) the start time, when said each crossing time is a first crossing time of said each baton, and (vi) send the determined split-times to an output device.

2. The system of claim 1, wherein:

the track map further specifies a location of a finish line of the running track;

the timing computer is configured to communicatively couple with a finish line timing computer to receive therefrom finish line timing information, and the timing computer is further configured to determine, for each baton, a final split time for a last leg of the relay race based on the finish line timing information and a last crossing time of said each baton.

3. The system of claim 2, the timing computer being further configured to receive the start signal from the finish line timing computer.

4. The system of claim 1, further including each baton.

5. The system of claim 4, each baton being coupled with two wireless tracking tags positioned at opposite ends of said each baton.

6. The system of claim 1, the timing computer including a filter for smoothing the determined movement of each baton.

7. The system of claim 1, the timing computer being further configured to determine a speed of each baton based on the periodically-determined locations of said each baton.

8. The system of claim 7, at least one of the wireless tracking tags comprising an accelerometer, wherein the timing computer is further configured to determine, based on data received from the accelerometer, a stride frequency of an athlete carrying a corresponding baton to which the accelerometer is coupled.

9. The system of claim 8, the timing computer being further configured to determine a stride length of the athlete based on the determined stride frequency and the determined speed of the corresponding baton.

* * * * *